United States Patent [19]
Castleman et al.

[11] 4,362,941
[45] Dec. 7, 1982

[54] APPARATUS AND A METHOD FOR DETECTING AND MEASURING TRACE GASES IN AIR OR OTHER GASEOUS BACKGROUND

[75] Inventors: B. Wayne Castleman, Kenneth City; Robert F. Donehoo, Clearwater, both of Fla.

[73] Assignee: Honeywell Inc., Minneapolis, Minn.

[21] Appl. No.: 228,407

[22] Filed: Jan. 26, 1981

[51] Int. Cl.³ .............................................. G01T 1/18
[52] U.S. Cl. .................................. 250/381; 250/382; 250/385
[58] Field of Search ............... 250/282, 288, 374, 381, 250/382, 384, 379, 386, 432 R; 315/108, 111.21, 111.81, 307; 324/464, 469

[56] References Cited
U.S. PATENT DOCUMENTS

| | | | |
|---|---|---|---|
| 2,994,768 | 8/1961 | Derfler | 250/381 |
| 3,835,328 | 9/1974 | Harris et al. | 250/432 R |
| 4,119,851 | 10/1978 | Castleman et al. | 250/282 |
| 4,238,678 | 12/1980 | Castleman et al. | 250/282 |

Primary Examiner—Alfred E. Smith
Assistant Examiner—Janice A. Howell

[57] ABSTRACT

An improved drift tube wherein the high voltage electric field is generated as a function of atmospheric pressure. Such variation of the electric field provides good compensation for the effects produced by changes in atmospheric pressure. As a result, the identification of a particular compound at different altitudes is greatly simplified.

6 Claims, 4 Drawing Figures

APPARATUS AND A METHOD FOR DETECTING AND MEASURING TRACE GASES IN AIR OR OTHER GASEOUS BACKGROUND

The present invention relates to apparatus for detection of small amounts of vapors or gases in an atmosphere of air or other gas. Specifically, the invention relates to an improvement in a drift tube type ionization sensor.

In a drift tube, vapors or gases are subjected to ionizing radiation and the resulting ions are placed in an electric field, causing the ions to migrate in a predetermined direction. The different types of ions can be separated, detected, and measured by virtue of the difference of velocity or mobility of the ions in an electric field. Ion shutters or gates are provided for segregating the ions in accordance with their drift time.

The construction of drift tubes can take several forms. In certain applications, two or more drift tubes are combined to increase selectivity and sensitivity. For example, U.S. Pat. No. 4,238,678 shows an apparatus where two drift tubes are combined in series. In one of the tubes, electric grids are provided and energized with constant potentials. The grids operate to capture lighter, higher mobility ions, while allowing a greater number of heavier, lower mobility ions to pass through. The second drift tube contains electric grids which are energized by electric potentials which are modulated. Through the application of the modulated potentials, the grids act as electric shutters, allowing packets to pass through at specified times, while blocking the passage of ions at other times.

Alternatively, the selectivity of vapors or gases can be improved by combining the features of a drift tube with that of an ionization cell, as illustrated in U.S. Pat. No. 4,119,851. The apparatus can take form in two basic configurations. In one configuration, the ionization cell operates as a pre-selector or pre-filter which eliminates or reduces the effects of the great majority of possible interfering ion species while allowing a significant fraction of the ions of interest to pass through. The drift tube then receives the selected ions and further classifies the ions on the basis of their mobility. In an alternate configuration, the drift tube is positioned upstream of the ionization cell.

The presence of particular ions in the vapor or gas is detected by appearance of an electric signal at the collector. The time separation or delay between the introduction of a packet of ions into a drift region and the detection of a signal at the collector provides the identifying information as to the ion type.

A problem encountered with the prior art drift tubes is caused by the fact that a shift occurs in the output signal with changes in atmospheric pressure. As the atmosphere pressure is decreased, the time delay between the introduction of a packet of ions into the drift region and its detection is reduced. The dependence of drift tube response on atmospheric pressure introduces ambiguity into the drift tube output signal information.

In accordance with the present invention, the high voltage electric field in the drift tube is varied as a function of atmospheric pressure. Such variation of the electric field provides good compensation for the effects produced by changes in atmospheric pressure. As a result, the identification of a particular compound at different altitudes or barometric pressures is greatly simplified.

It is therefore an object of the present invention to provide an improved drift tube with compensation for changes in atmospheric pressure. A more specific object of the present invention is to provide an ionization sensor which is capable of unambiguously identifying a particular compound under conditions of different atmospheric pressures. A further object of the present invention is to provide an improved ionization sensor capable of being operated at any altitude, with automatic compensation for variations in atmospheric pressure due to changes in altitude.

DESCRIPTION OF THE PREFERRED EMBODIMENTS

Figure 1:
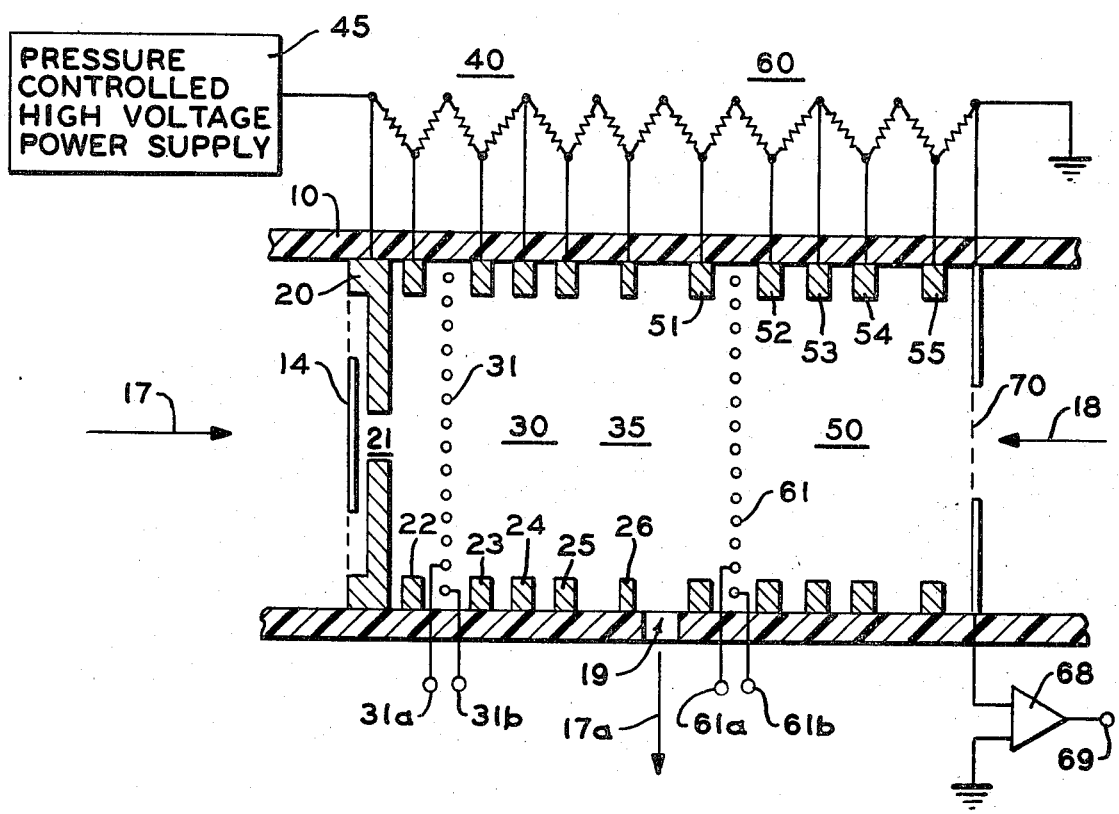
FIG. 1 of the drawings illustrate a preferred embodiment of the present invention.

Referring to FIG. 1 of the drawing, a preferred embodiment of the present invention is shown having a housing 10 constructed of non-conductive material, such as Teflon or constructed of a conductive material, such as aluminum, lined or coated with a non-conductive material. Mounted within housing 10, at a first end, is a radiation emitting source 14, which consists of a metal screen to which is affixed a radiation emitting foil. The gas sample to be detected is received from the direction shown by arrow 17. A conductive plate 20, having a central opening 21, separates radiation source 14 from a drift region 30. The other end of drift region 30 (the downstream end) is defined by a region 35 wherein the sample gas stream combines with the flow of clean air or gas from the direction indicated by arrow 18.

Figure 4:
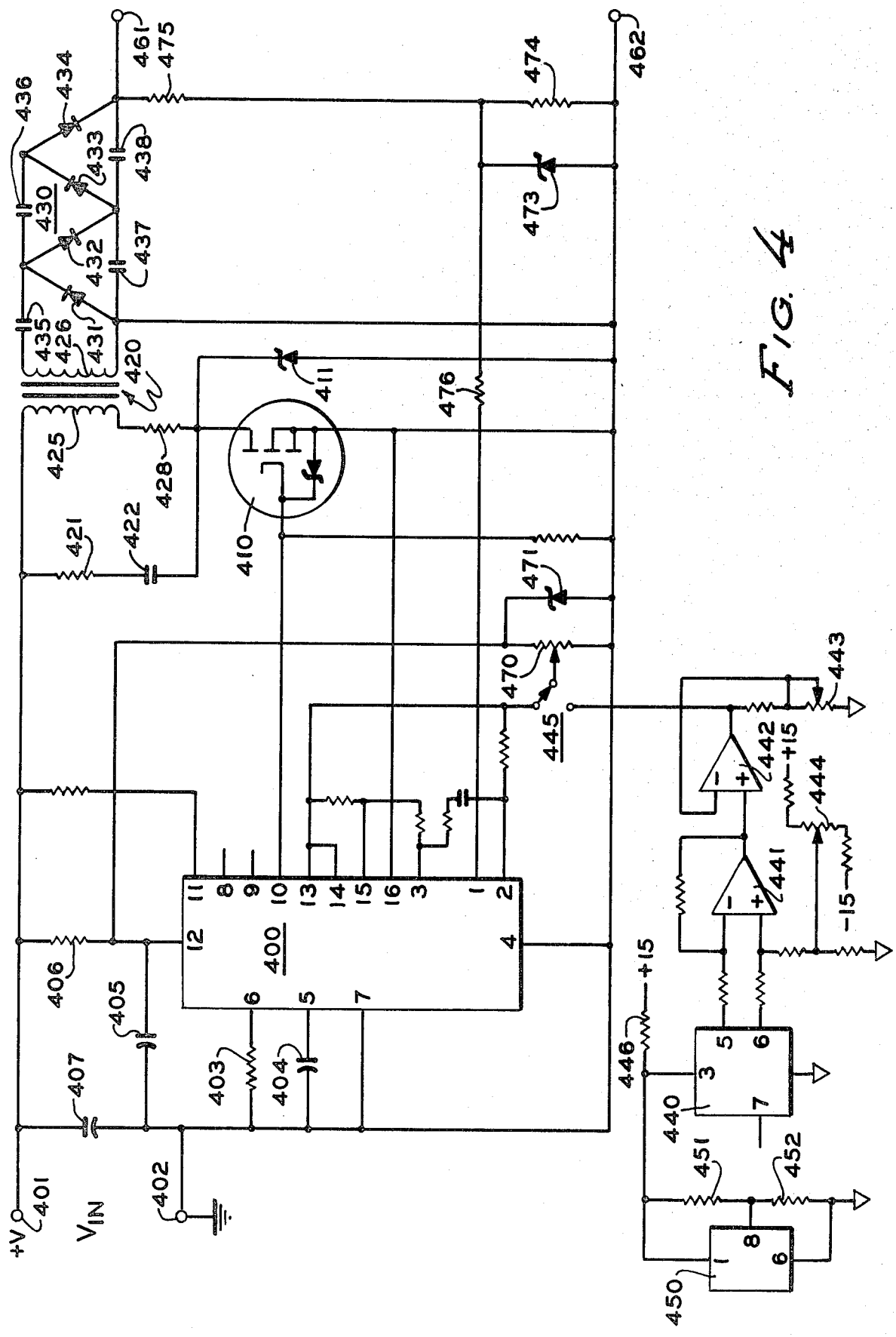
FIG. 4 is a schematic diagram of a power supply whose voltage output varies with changes in atmospheric pressure.

A plurality of conductive rings 22, 23, 24, 25, and 26 are mounted within drift region 30 and are connected to an electric potential source 45 via a voltage divider network 40. Electric potential source 45, in conjunction with voltage divider network 40, establishes a linear electric field between plate 20 at the upstream end and conductive ring 26 at the downstream end of drift region 30. The intensity of the linear electric field is varied as a function of atmospheric pressure to compensate for the effects produced in the output signal due to pressure change. Electric potential source 45 is a pressure controlled high voltage power supply, such as shown in FIG. 4.

An electrically conductive grid 31 is positioned in a plane normal to the gas flow between guard rings 22 and 23 near the upstream end of drift region 30. Grid 31 is comprised of a plurality of electric conductors, the alternate of which are connected to each other such that a different voltage can be applied to alternate conductors in each grid at terminals 31a and 31b, respectively.

A second drift region identified with numeral 50 is located downstream from drift region 30. In drift region 50, electrically conductive guard rings 51, 52, 53, 54, and 55 are mounted about the periphery of the drift region in the manner shown. A collector electrode 70 is mounted in a plane perpendicular to the direction of gas flow at the downstream end of drift region 50. A voltage divider network 60 connects guard rings 51 through 55 and collector electrode 70 to electric potential source 45 via voltage divider network 40. Electric potential source 45, together with divider network 40, establishes a linear electric field in drift region 50 between guard ring 51 and collector 70.

A counter flow of clean air flows continuously in the direction shown by arrow 18 and serves to prevent ion-molecule reactions from occurring in drift region 50. The two streams of gas combine in region 35 and the resulting gas mixture is pumped out through port 19 in the direction shown by arrow 17a. In an alternate and equally effective mode of operation, the gas sample can be introduced through port 19 in a direction opposite arrow 17a and the two gas streams (17a reversed and 18) will combine and be pumped out from the left side of housing 10 in a direction opposite arrow 17.

A grid 61 is positioned in drift region 50 between guard rings 51 and 52 in a plane normal to the direction of gas flow. As in the case of grid 31 in drift region 30, grid 61 has alternate conductors electrically connected to each other such that the alternate conductors can be energized with different voltage at terminals 61a and 61b, respectively.

Collector electrode 70 is connected to the input of an amplifier 68, which has an output 69.

In the preferred embodiment of the invention shown in the drawing, the gas sample is received from the direction of arrow 17 and is directed past radioactive source 14 into drift region 30. The gas sample becomes ionized near the radioactive source 14 by a charge transfer process. The resulting ions move under the influence of a constant potential established in region 30. A further much lesser influence on the motion of the ions is the constant flow of the gas through the tube. Grid 31 is operated as a co-planar electrical shutter. By applying appropriate constant potentials to terminals 31a and 31b of grid 31, the shutter is biased partially open to allow only ions of lower mobility to enter into drift region 30. Grid 31, with the difference potentials between the alternate conductors, acts very much like the recombination region of an ionization cell such as shown in U.S. Pat. No. 3,835,328, to Harris, et al. issued on Sept. 10, 1974. That is, the grid operates as an electrical analog to baffles, providing a means for capturing the lighter, higher mobility ions, while allowing a greater number of heavier, lower mobility ions to pass through to the second drift tube. A major advantage of using grid 31 in the manner described, as opposed to passing ions through a recombination region, is that a much greater concentration of ions survive and reach grid 61. The sensitivity and stability of the cell are thereby improved.

The ions emerging from drive region 30 enter drift region 50. As stated previously, a linear electric field is established in drift region 50 by electric potential source 45 through divider networks 40 and 60, connected to guard rings 51 through 55 and collector 70. The alternate conductors in grid 61 are energized such that a different potential can briefly exist between adjacent conductors, while the average potential of each grid is equal to the linear drift potential at the location of the respective grid. The ions emerging from drift region 30 and passing through region 35 (wherein the gas streams combine) reach grid 61 in a steady stream. By applying appropriate potentials to terminals 61a and 61b of grid 61, the shutter opens briefly to allow a discrete packet of ions to enter drift region 50. Each ion species drifts at a speed which is characteristic of its mobility. Therefore, when several ion species are present they can be separately detected by their different arrival times at collector 70.

Collector 70 is connected to the input of an amplifier 68, whose output 69 will provide the signal indicating the presence of particular ions in the gas sample. The amplitude of the signal is a function of the number of ions detected.

In the operation of the preferred embodiment described above, grid 31 in recombination region 30 was energized with constant potentials, while grid 61 of recombination region 50 was energized with modulated potentials. The invention operates satisfactorily with the functions of the two drift cells reversed, i.e. by energizing grid 31 with modulated potentials and applying constant potentials to grid 61.

While in the preferred embodiment of the present invention drift regions 30 and 50 are shown to be of about the same size, the invention works equally well with drift regions of different sizes, both in length and diameter. The placement of grid 31 and the constant potentials applied thereto can be selected to obtain a particular desired effect on the ion species produced and transmitted through region 30.

Figure 2:
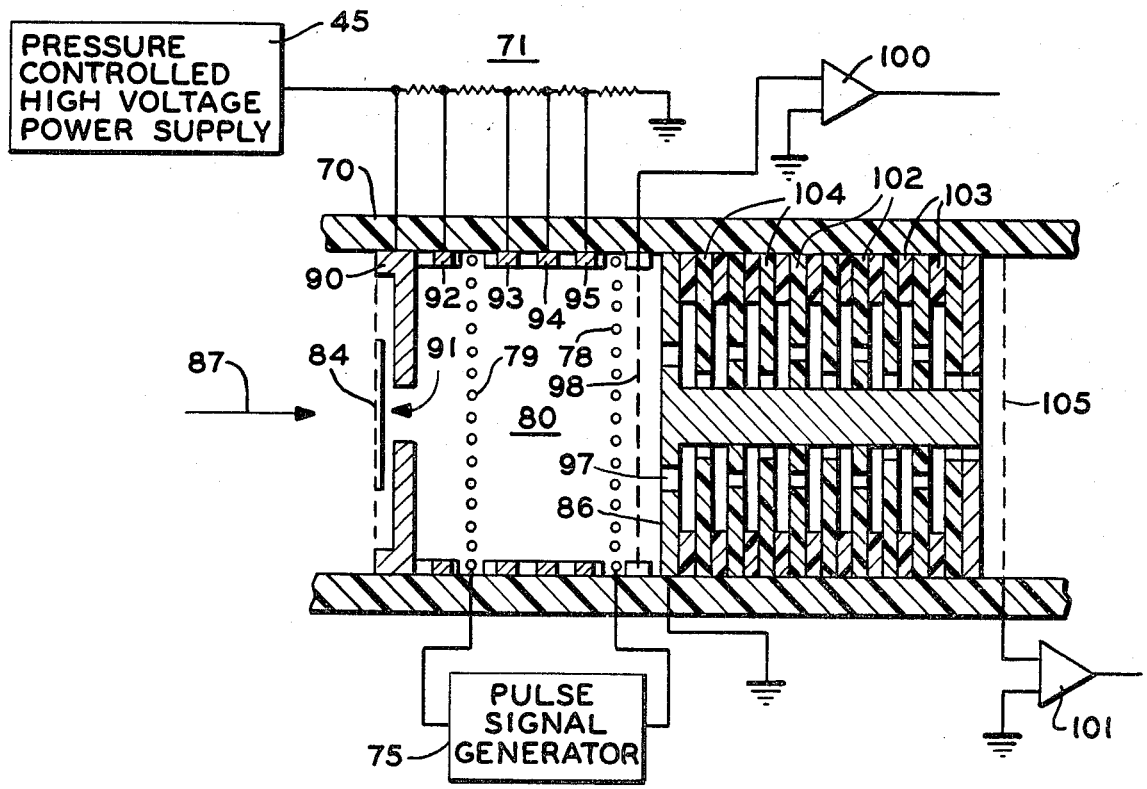
FIG. 2 illustrates an alternate embodiment of the present invention.
Figure 3:
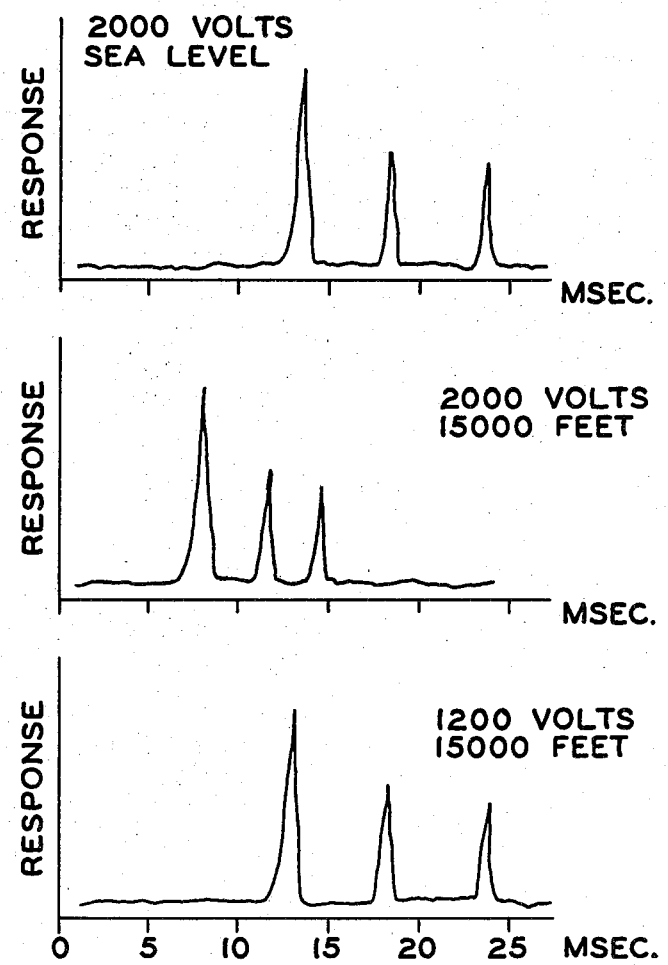
FIG. 3 is a graphical representation of the changes in signals generated by cells such as shown in FIGS. 1 and 2 as a function of changes in altitude and voltage.

FIG. 3 is a graphical representation of the variations in the signals appearing at the outputs of the cells of FIGS. 1 and 2 as a function of changes in voltage and altitude. The upper curve of the graph shows the response to dimethyl methyl phosphonate (DMMP) at sea level with the high voltage at the output of power supply 45 at 2000 volts. The second curve from the top shows the response to DMMP at 15,000 feet altitude (about 0.6 sea level pressure) at 2000 volts. It should be noted that all spectral peaks move, but not equally. The lower curve of FIG. 3 shows the response to DMMP at 15,000 feet altitude but with the voltage reduced to approximately 1200 volts. The resulting response is virtually identical to sea level response at 2000 volts. Thus, using the compensation technique of the present invention, DMMP can be reliably identified at different altitudes.

FIG. 2 illustrates an alternate preferred embodiment of the present invention. It includes a housing 76 constructed of non-conductive material, such as Teflon. Mounted within housing 76, at a first end, is a radiation emitting source 84, which consists of a metal screen to which is affixed a radiation emitting foil. A conductive plate 90, having a central opening 91, separates radiation source 84 from a drift region 80. The other end of drift region 80 (the downstream end) is defined by a manifold 86, which also defines the upstream end of a recombination region. A plurality of conductive rings 92, 93, 94, and 95 are mounted within drift region 80 and are connected to a source of a pressure controlled high voltage power supply 45 via voltage divider network 71 to establish a linear electric field between plate 90 and manifold 86. Electrically conductive grids 79 and 78 act as electrical shutters which, upon receiving an appropriate signal from pulse signal generator 75 allow only ions of a specific mobility to pass through the drift region and into the recombination region beyond manifold 86.

The voltage supplied to rings 92 through 95 from power supply 45 is varied with changes in atmospheric pressure to provide compensation for such changes in pressure. Power supply 45 can be of the type shown in FIG. 4 and described below.

The selected ions which are allowed to pass through drift region 80 are then further acted upon in the recombination region by interaction with surfaces created by washers 103 and baffles 104 and 102 and manifold 86.

The ions exiting drift region 80 generate a signal at collector 98 which is received at the input of amplifier 100. The ions passing through the recombination region and reaching collector 105 at the downstream end of the recombination region generate a signal which is applied to the input of amplifier 101. The amplified signals from amplifiers 100 and 101 may be used individually as an indication of the presence of specific ions in the gas sample, or these signals can be logically combined for increased sensitivity.

The schematic of a pressure controlled high voltage power supply used in the preferred embodiment of the present invention is illustrated in FIG. 4. The input voltage to the power supply is applied between input terminals 401 and 402. Normally, the input voltage is derived from a source such as a battery operating between 20 and 36 volts. The power supply converts this relatively low input voltage into a high voltage output in the range of 2000 volts, appearing between output terminals 461 and 462.

A PWM (pulse width modulator) 400 drives a VMOS switch 410 connected in series with a primary winding 425 of a transformer 420. Transformer 420 has a secondary winding 426 which has a turns ratio of about 20 to 1 as compared to primary winding 425. Resistor 421 and capacitor 422, connected across primary winding 425, form what is commonly referred to as a snubber circuit. Its function is to limit the voltage across winding 425 during the "flyback" action. A small resistor 428 is connected between winding 425 and VMOS switch 410. Its function is to act as a fuze in case of excessive current flow, to prevent damage to VMOS switch 410 or zener diode 411. A zener diode 411 is connected across VMOS switch 410 to keep the voltage across VMOS 410 from rising above 75 volts and prevent voltage breakdown of the switch.

The amplified voltage appearing across secondary winding 426 is further stepped up through a diode/capacitor voltage multiplier network 430 comprised of diodes 431 through 434 and capacitors 435 through 438.

Pulse width modulator 400 in the preferred embodiment is an integrated circuit TL494 manufactured by Texas Instruments. Other equivalent circuits available on the market could be used for this purpose.

The power to PWM 400 is applied between pins 7 and 12, pin 12 being connected through resistor 406 to the positive potential terminal 401 and pin 7 being connected to the reference potential terminal 402. Resistor 403 and capacitor 404, connected between pins 6 and 5, respectively, and the ground potential terminal 402, set the operating frequency of PWM 400.

A capacitor 407 connected between input terminals 401 and 402 provides localized filtering to supply transient current for the switching circuit and absorb voltage transients generated by it. Resistor 406 and a capacitor 405 form a decoupling circuit.

The output of PWM 400, which is applied to the base electrode of VMOS switch 410, is provided at pin 10.

Pin 1 of pulse width modulator 400 is connected to a junction point between resistor 474 having its other end connected to output terminal 461 and resistor 475 having its other end connected to output terminal 462. The signal received by pin 1, which is a function of the output voltage appearing between output terminals 461 and 462, is compared internally in circuit 400 with a reference voltage signal applied at pin 2. The difference in the voltages received at pins 1 and 2 controls the duty cycle of PWM 400, which in turn controls the amplitude of the output voltage between terminals 461 and 462 through the operation of VMOS switch 410. Via a switch 445, pin 2 of PWM 400 can be connected to either receive a manually selected reference voltage from a variable voltage divider 470 or a pressure controlled voltage generated by pressure transducer 440. A zener diode 471 sets the voltage across voltage divider 470. A second zener diode 473 is connected across resistor 474 to provide over voltage protection for PWM 400 input.

In the preferred embodiment, pressure transducer 440 is a piezoresistive type manufactured by National Semiconductor and identified by LX0503A. Other comparable pressure transducers are available on the market. Pressure transducer 440 has constructed internally a resistive bridge comprised of piezoresistive elements. The output voltage signal appearing between pins 5 and 6 of transducer 440 is a differential signal indicative of the bridge unbalance produced by changes in pressure. The signal from the output of transducer 440 is applied between input terminals of a differential amplifier 441, where it is amplified and then applied to the input of a second amplifier 442. The signal from the output of amplifier 442 is a pressure responsive voltage signal which can be applied to pin 2 of PWM 400 through switch 445. When switch 445 is moved into the position connecting the output of amplifier 442 to pin 2 of PWM 400, the duty cycle of PWM 400 will be controlled as a function of atmospheric pressure.

Pressure transducer 440 is connected to receive input power between pin 3 connected to a positive potential source through resistor 446 and pin 8 connected to ground. The input voltage between pins 3 and 8 is accurately controlled by adjustable precision shunt regulator 450, which in the preferred embodiment is a TL431 type manufactured by Texas Instruments. Resistors 451 and 452 are selected to control the voltage at pin 3 at approximately 6.5 volts.

A variable resistor 443 is connected between the output of amplifier 442 and the ground terminal for calibrating the pressure variable reference voltage applied to pin 2 of PWM 400. In the preferred embodiment, variable resistor 20 is adjusted such that at a pressure of 1 atmosphere the power supply generates 2000 volts between output terminals 461 and 462.

A unique and improved apparatus for sensing and measuring gaseous impurities has been shown and described in the foregoing specification. Various modifications of the inventive concepts will be obvious to those skilled in the art, without departing from the spirit of the invention. It is intended that the scope of the invention be limited only by the following claims.

We claim:

1. An apparatus for detecting trace amounts of vapors or gases in air or other gaseous backgrounds, said apparatus comprising:
 a housing defining a passage for flow of gas through a drift region;
 a source of ionizing radiation positioned in said passage near a first end of said drift region for creating ions in said gas;

a collector electrode mounted within said passage near a second end of said drift region;

means for establishing a substantially linear drift potential in said housing for causing said ions to move through said drift region from said source of ionizing radiation toward said collector electrode;

means for varying said drift potential as a function of atmospheric pressure;

means for gating discrete packets of ions into said drift region; and means for detecting the ions reaching said collector electrode.

2. An apparatus for detecting trace amounts of vapors or gases in air or other gaseous backgrounds, said apparatus comprising:

a housing defining a passage for flow of gas through first and second drift regions;

a source of ionizing radiation positioned in said passage near said first drift region for creating ions in said gas;

a collector electrode mounted within said housing near said second drift region;

means for establishing a substantially linear drift potential in said housing for causing said ions to drift from said source of ionizing radiation toward said collector electrode through said first and second drift regions;

means for varying said drift potential as a function of atmospheric pressure;

an electrically conductive grid means located in said first drift region, said grid being comprised of a plurality of conductors biased at predetermined constant electric potentials for selectively collecting ions of higher mobility, while allowing lower mobility ions to pass through to said second drift region;

gating means located in said second drift region for allowing selected groups of ions from said first drift region to pass through into said second drift region and onto said collector electrode at times proportional to their mobility;

means for measuring the number of ions reaching said collector electrode.

3. Apparatus according to claim 2, wherein said gating means is comprised of a plurality of conductors, alternate of said conductors being connected to first and second terminals, whereby said gating means can be operated by application of appropriate potentials to said terminals to allow discrete packets of ions to enter into said second drift region.

4. Apparatus according to claim 2, wherein said gating means is located in said first drift region and said electrically conductive grid means is located in said second drift region.

5. Apparatus according to claim 3, wherein said gating means is comprised of a plurality of conductors, alternate of said conductors being connected to first and second terminals, whereby said gating means can be operated by application of appropriate potentials to said terminals to allow discrete packets of ions to enter into said first drift region.

6. Apparatus for detecting trace amounts of vapors or gases in air or other gaseous backgrounds, said apparatus comprising:

a housing defining a passage for flow of gas between an input and an output;

a source of ionizing radiation positioned in said passage near said input for creating ions in said gas;

a recombination region defined by first portion of said passage between said source of ionizing radiation and said output, said recombination region including means for facilitating recombination of ions in said gas entering the recombination region;

a drift region defined by a second portion of said passage between said source of ionizing radiation and said output, said drift region including a collector electrode, means for establishing a drift potential for causing said ions to drift toward said collector electrode, means for varying said drift potential as a function of atmospheric pressure, and gating means for allowing only ions of predetermined mobility to reach said collector electrode.

* * * * *